(12) United States Patent
Bala

(10) Patent No.: US 7,718,125 B2
(45) Date of Patent: May 18, 2010

(54) STERILIZATION CHALLENGE SPECIMEN HOLDER

(75) Inventor: Harry Bala, South Barrington, IL (US)

(73) Assignee: Dana Products Inc., Franklin Park, IL (US)

( * ) Notice: Subject to any disclaimer, the term of this patent is extended or adjusted under 35 U.S.C. 154(b) by 361 days.

(21) Appl. No.: 11/828,202

(22) Filed: Jul. 25, 2007

(65) Prior Publication Data

US 2009/0029451 A1 Jan. 29, 2009

(51) Int. Cl.
*C12M 1/12* (2006.01)

(52) U.S. Cl. .............. 422/58; 422/50; 422/56; 422/61; 422/102; 436/1; 435/31; 435/287.4

(58) Field of Classification Search ............... 422/30, 422/58, 59, 61, 99, 102, 104; 206/305
See application file for complete search history.

(56) References Cited

U.S. PATENT DOCUMENTS

| | | | |
|---|---|---|---|
| 3,114,349 A | 12/1963 | Schuman | |
| 3,313,266 A | 4/1967 | Kelson | |
| 3,341,238 A | 9/1967 | White | |
| D222,516 S | 10/1971 | Kelson | |
| 3,652,249 A | 3/1972 | White | |
| 3,951,333 A | 4/1976 | Forbes, Jr. et al. | |
| 3,981,683 A | 9/1976 | Larsson et al. | |
| 3,991,881 A | 11/1976 | Augurt | |
| 4,221,307 A * | 9/1980 | Peterson | 222/428 |
| 4,448,548 A | 5/1984 | Foley | |
| 4,486,387 A | 12/1984 | Augurt | |
| 4,576,795 A | 3/1986 | Bruso | |
| 4,579,715 A | 4/1986 | Bruso | |
| 4,594,223 A | 6/1986 | Dyke et al. | |
| 4,596,696 A | 6/1986 | Scoville, Jr. | |
| 4,636,472 A | 1/1987 | Bruso | |
| 4,692,307 A | 9/1987 | Bruso | |
| 4,699,765 A | 10/1987 | Hambleton | |
| 4,883,641 A * | 11/1989 | Wicks et al. | 422/58 |
| 5,200,147 A | 4/1993 | Augurt | |
| 5,204,062 A | 4/1993 | Buglino et al. | |
| 5,418,167 A * | 5/1995 | Matner et al. | 422/58 |
| 5,514,341 A * | 5/1996 | Urata et al. | 422/58 |

(Continued)

FOREIGN PATENT DOCUMENTS

DE 4319395 C1 * 4/1995 ............ 422/50

(Continued)

OTHER PUBLICATIONS

International Search Report for PCT/US08/69939, Oct. 3, 2008.

*Primary Examiner*—Jill Warden
*Assistant Examiner*—Sharon Pregler
(74) *Attorney, Agent, or Firm*—Levenfeld Pearlstein, LLC

(57) ABSTRACT

A sterilization challenge specimen holder is used with a test indicator to challenge sterilization on a consistent basis. The holder includes a body having an internal chamber region. A cap is sealable on the holder. A plug is positioned in the body. The plug has a wall having a spiral formed groove therein in communication with the internal chamber region. An opening provides for a single flow path for communication between the environs and the internal chamber via the groove.

19 Claims, 6 Drawing Sheets

U.S. PATENT DOCUMENTS

| | | | | |
|---|---|---|---|---|
| 5,543,115 | A * | 8/1996 | Karakawa | 422/58 |
| 7,090,808 | B2 * | 8/2006 | Caputo et al. | 422/305 |
| 7,091,035 | B2 * | 8/2006 | Ravin et al. | 435/288.3 |
| 2002/0034823 | A1 * | 3/2002 | Kuepper et al. | 422/58 |
| 2003/0133837 | A1 * | 7/2003 | Bancroft | 422/58 |
| 2003/0190259 | A1 * | 10/2003 | Alley | 422/58 |
| 2005/0029306 | A1 * | 2/2005 | Brennan | 222/327 |
| 2006/0263245 | A1 * | 11/2006 | Watanabe et al. | 422/58 |
| 2009/0029451 | A1 * | 1/2009 | Bala | 435/287.4 |

FOREIGN PATENT DOCUMENTS

| | | | | |
|---|---|---|---|---|
| DE | 4319397 | C1 * | 4/1995 | 422/50 |

* cited by examiner

STERILIZATION CHALLENGE SPECIMEN HOLDER

BACKGROUND OF THE INVENTION

The present invention is directed to a sterilization challenge specimen holder. More particularly, the present invention pertains to a reusable specimen holder for challenge in a sterilization environment.

The sterilization of medical equipment, towels (for hospital and operating room use), gowns and the like is carried out, for the most part, using steam sterilization equipment and methods. For example, a bundle of towels is placed into a steam sterilizer, a vacuum is drawn in the sterilizer to evacuate the air, and steam is introduced to sterilize the bundle of towels.

Due to the nature of the towels being "bundled" it may be difficult to assure that the innermost regions (volume) of the towels have been sufficiently subjected to the steam (time and temperature) to assure proper levels of sterilization. Essentially, it is a "challenge" for the steam to be introduced to the innermost parts to effect sterilization.

To this end, "challenge packs" or "challenge kits" have been created to simulate the bundle and more specifically to simulate the difficulty or resistance in reaching the innermost parts: (1) to effect a vacuum; and (2) to introduce steam sufficient to sterilize the local area. There is in fact an ANSI standard for challenge packs that is based upon a bundle of towels having a specific size.

Presently, there are challenge packs on the market. These include paper stacks (stacked like a deck of cards) with an indicator sheet generally in the middle of the stack that can indicate either that a vacuum has been achieved or that a sufficient amount of steam has reached the indicator pack. Another includes a paper stack with a cut out center with a biological indicator vile in the middle. Still another type of indicator includes a plastic tube that has a hole in one end, is packed with a permeable material (such as a towel or absorbent paper sheet) and an indicator at the opposite end.

All of these challenge packs are one time use, disposable products. Various indicators (e.g., for use in the middle of the stack or for other types of uses) can be used in different environments and situations and provide indication of vacuum, biological activity (or inactivity) or steam contact.

Accordingly, there is a need for a challenge device that provide sufficient challenge to sterilization on a consistent basis. Desirably, such a device is easy to use and does not require additional packing materials (towel bundles). More desirably, such a device is reusable with disposable (one-time use) indicators. Most desirably such a device is a passive device (e.g., no moving mechanical and/or electro-mechanical components).

BRIEF SUMMARY OF THE INVENTION

A sterilization challenge specimen holder is used with a disposable (one-time use) indicator, such as a biological indicator. The holder includes a body having an internal chamber region and a cap sealable on a first end of the body. The cap can be threaded and include seal to isolate the internal chamber region.

A plug is positioned in a second end of the body. The plug has an outer wall that has a spiral formed groove therein. A lower end of the groove opens into (is in communication with) the internal chamber region. The plug has an opening therein that define a single flow path for communication between the environs and the internal chamber via groove.

In a present embodiment, the body has a smooth inner wall at the second or plug end and the plug is shrink fitted into the end of the body.

To assure a consistent flow path between the internal chamber region and the environs, the groove is formed having a rounded root area. In a present holder, the groove has a cross-sectional area of less than about 5.5 E-4, about 3.0 E-4 to about 5.5 E-4 $in^2$, and preferably about 3.0 E-4 $in^2$, with a depth of about 0.011 in.

To effect a smooth transition from the groove to the internal chamber region, the plug includes a chamfer at an end of the plug innermost of the chamber such that the lower end of the groove terminates at the chamfer. The plug can also include a well formed therein that defines a wall in the plug. An opening in the wall provides communication between the environs and the internal chamber region through the groove. In this arrangement, the plug can include a peripheral recess in the wall adjacent to the groove such that the opening penetrates the wall at the recess. An upper end of the groove terminates at the recess and a chamfer is formed in the recess such that the upper end of the groove terminates at the chamfer.

To assure a proper fit of and seal between the plug and body, the plug and body are formed from materials that have similar thermal expansion coefficients, and preferably, similar materials, such as aluminum.

The facilitate handling, the cap can have a knurled edge and to prevent the holder from rolling the edge can have a flat region formed thereon.

The holder can also include an insulating layer on at least a portion of the body.

The plug can be configured with a pressure reducing element to reduced the pressure of the steam entering the holder.

Alternately, the plug can be configured as a flat split disk-like element having a flat spiral formed groove in one portion of the disk-like element with the other portion of the disk-like element covering the flat spiral groove. The groove is in communication with the internal chamber region and the disk-like element has an opening therein to the environs for defining a single flow path for communication between the environs and the internal chamber via the groove.

In still another embodiment, the holder includes a body having an internal chamber region and a plug positioned in part in the body. The plug has a central bore and an outer wall having the spiral formed groove in the outer wall. The groove is in communication with the internal chamber region. In this embodiment, the body has an opening for defining a single flow path for communication between the environs and the internal chamber via the spiral formed groove. A cap is sealable on the plug of the end of the plug external to the holder body to seal the holder. Alternately still, the groove can be formed in the body of the holder and the plug can be smooth-walled.

These and other features and advantages of the present invention will be apparent from the following detailed description, in conjunction with the appended claims.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein.

DETAILED DESCRIPTION OF THE INVENTION

Figure 1:
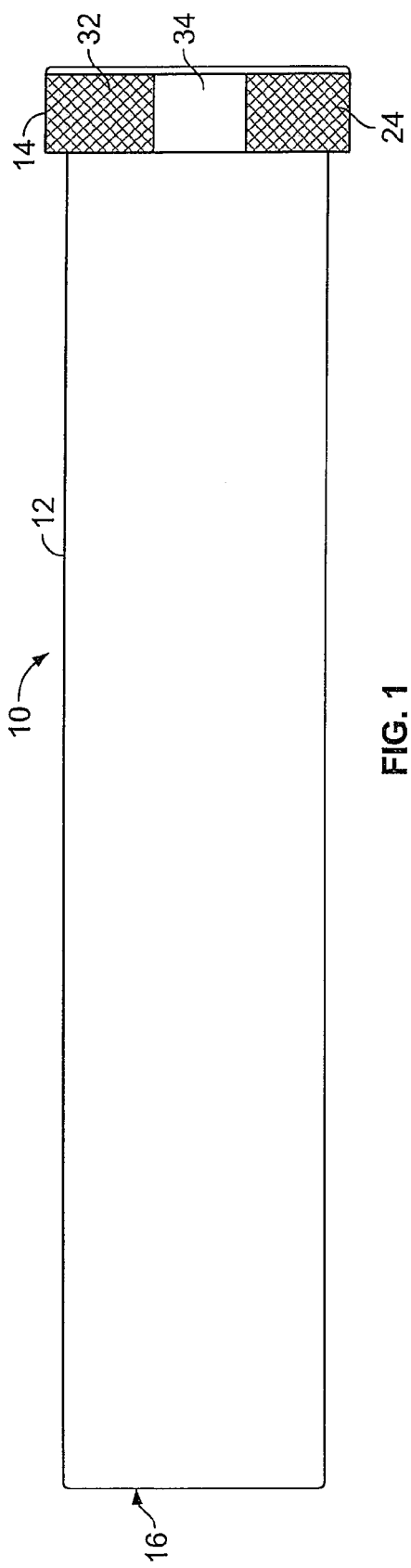
FIG. 1 is a plan view of a sterilization challenge specimen holder embodying the principles of the present invention.
Figure 2:
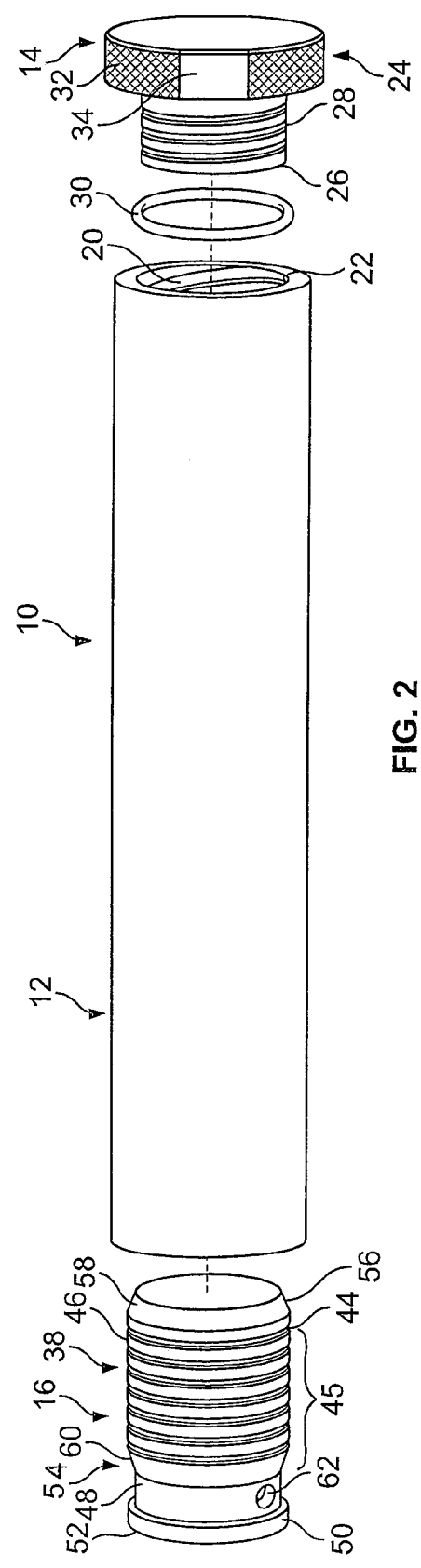
FIG. 2 is an exploded view of the specimen holder of FIG. 1.
Figure 3:
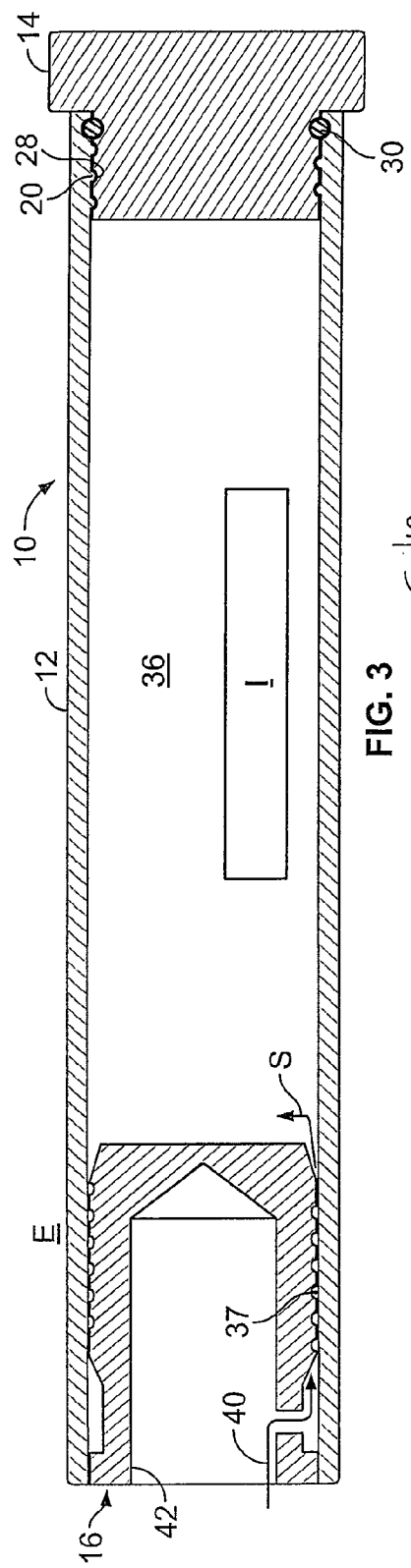
FIG. 3 is a cross-sectional view taken along line 3-3 of FIG. 1.
Figure 4:
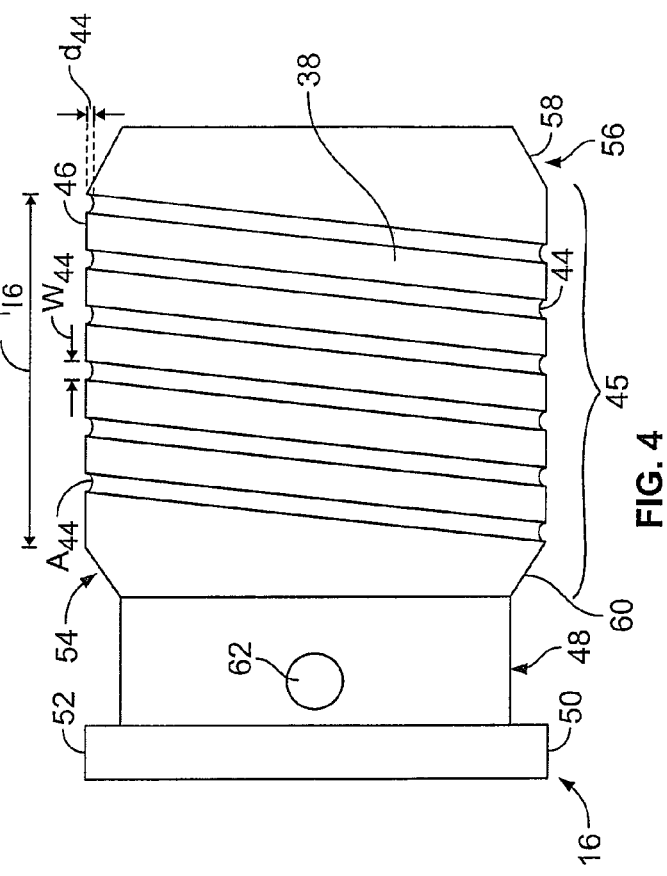
FIG. 4 is an enlarged view of the end plug of the holder.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description Of The Invention", relates to a requirement of the United States Patent Office, and does not imply, nor should be inferred to limit the subject matter disclosed herein.

Figure 5:
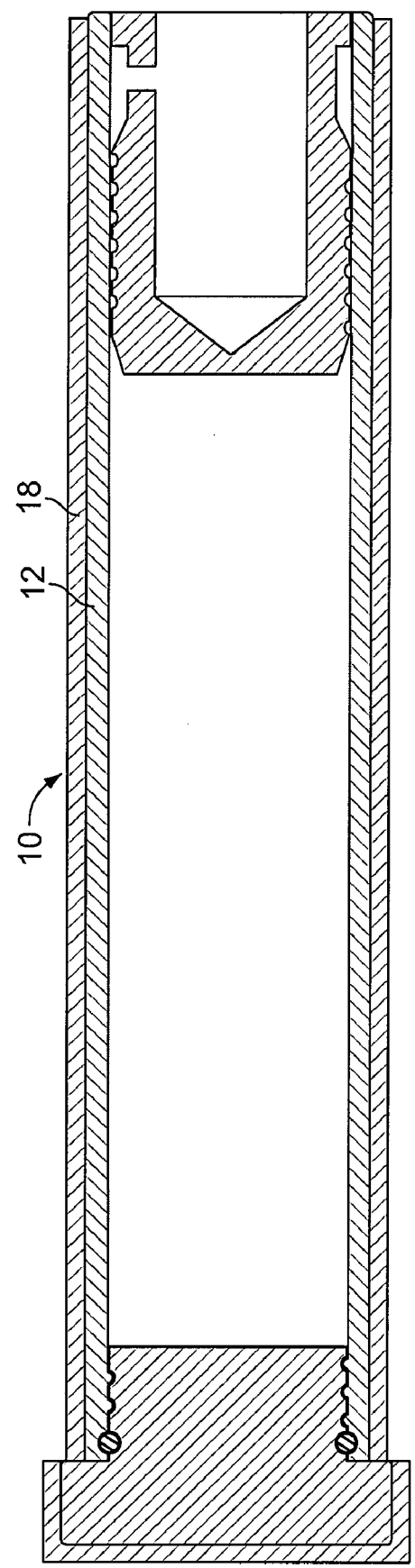
FIG. 5 is a cross-sectional view of the specimen holder showing an optional insulating layer on the holder.

Referring to the figures and in particular to FIG. 1 there is shown a sterilization challenge specimen holder 10 embodying the principles of the present invention. The holder 10 includes a hollow tubular body 12, a closure cap 14 and an end plug 16. The body 12 can be covered or enveloped in an insulating layer 18 (as seen in FIG. 5).

The body 12 includes an internal thread 20 at one open end 22. The closure cap 14 includes a gripping portion 24 and a depending plug 26 having an external thread 28 (to mate to the threaded 20 opening) to close the holder 10. A seal 30 such as the illustrated O-ring can fitted onto the cap 14 to provide a gas-tight seal between the closure cap 14 and the body 12. In a present holder 10, the gripping portion 24 is textured or knurled (as indicated at 32) to facilitate rotating or turning the cap 14. The gripping portion 24 can include a flattened portion (a flat 34) so that when the holder 10 is laid on its side, it will be prevented from rolling.

Figure 6:
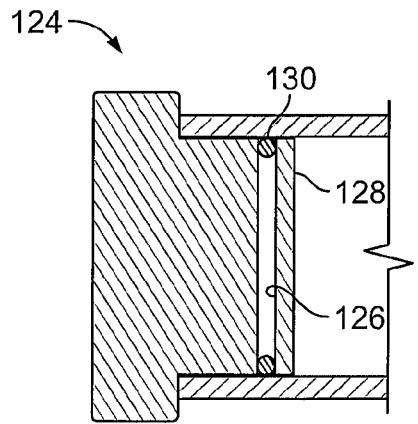
FIG. 6 is a partial cross-sectional view of an alternate end cap configuration.

Alternately, as seen in FIG. 6, the closure cap 124 can have an O-ring 130 seal in a channel or 128 in the plug portion 126 in a friction fit or push-in configuration. This eliminates the need for a threaded end in the cap 124.

The end plug 16 is of a novel configuration and provides a single ingress and egress flow path into and out of the interior or chamber 36 when the cap 14 is in place on the body 12 and permits drawing a vacuum in the holder 10 and introducing a sterilization fluid, such as steam, into the holder 10 in a controlled manner. The plug 16 includes a body 38 having a recess or well 40 formed therein that defines an inner wall 42. The body 38 includes a spiral formed channel or groove 44 in an outer wall 46 thereof. The outer wall 46 includes a peripheral recess or channel 48 formed adjacent to a sealing lip 50 at an end 52 of the plug 16.

The spiral formed channel 44 opens at a first end 54 into the peripheral recess 48 and spirals around the body 38 extending to about the opposite end 56 of the plug 16. In a present plug 16, the opposite end 56 (which is the end at the chamber 36 side of the plug 16), includes a chamfer 58 at which the spiral formed groove 44 ends. In a present plug 16, the transition from the peripheral channel 48 to the grooved region 45 is also chamfered as indicated at 60.

The plug 16 includes an opening 62 through the wall 46 at the peripheral recess 48. The opening 62 provides communication between outside of the holder 10 (the environs E) and the interior or chamber 36 of the holder 10. Communication is provided from the environs E, through the opening 62, into the recess 48, through the spiral groove 44 and into the chamber 36. The chamfers 58, 60 at both ends of the spiral groove 44 (or grooved region 45) provide for a smooth transition into and out of the groove 44 and prevent excessive resistance to flow through the groove 44.

The plug 16 is friction fitted into the chamber body 12. In this manner the lip 50 is snug up to the interior wall 37 of the body 12 and provides an external seal between the environs E and the peripheral recess 48. Moreover the plug body outer wall 46, at the grooved region 45 (between the chamfers 58, 60) also is snug up to the interior wall 37 of the body 12 and provides a seal between the recess 48 and the chamber 36 and the groove 44. It will be appreciated that the interior wall 37 of the body, at the plug 16 is smooth, unlike the threads 20 formed in the cap 14 end. In that there is no machining necessary at interior wall 37 the smooth surface (unlike threads) proper "mating" of the plug 16 and body 12 is enhanced.

Figure 7:
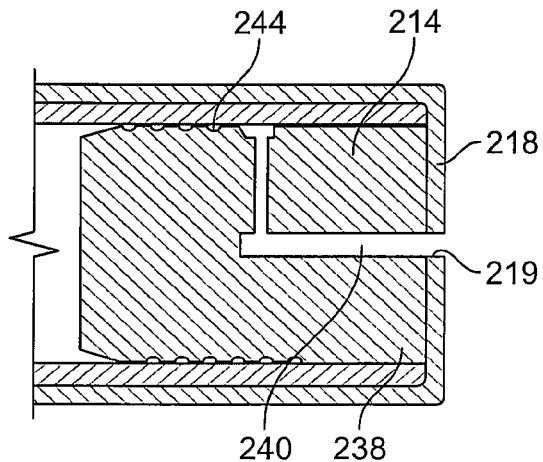
FIG. 7 is a partial cross-sectional view of an alternate plug configuration.

An alternate plug 216 is shown in FIG. 7. The plug 216 includes a channel 240 through the plug body 238 that is contiguous with the groove 244. In this manner, the plug 216 can be insulated, as indicated at 218. An opening 219 in the insulating layer 218 provides communication into the channel 240 and groove 244.

Figure 8:
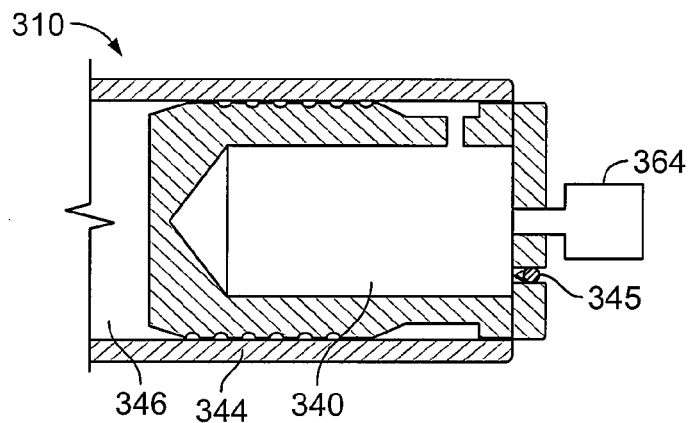
FIG. 8 is a partial cross-sectional view of a plug having a pressure reducer mounted thereto.

Alternately still, as seen in FIG. 8, the holder 310 can be fitted with a pressure reducing valve 364 to reduce the pressure (and thus the flow rate) of steam into the well 340 and thus through the groove 344 into the chamber 346. The reduced flow rate does not effect the steam temperature, but reduces the pressure to provide less driving force for flow (less driving force by virtue of less pressure differential). A check valve 345 permits evacuation of the chamber 346 prior to steam introduction or during the sterilization process.

Figure 9A:
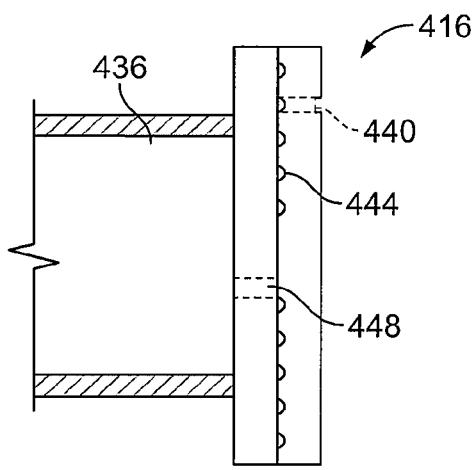
FIGS. 9A and 9B are partial cross-sectional and plan views of still another alternate plug design using a flat disk with a spiral planar spiral formed groove.
Figure 9B:
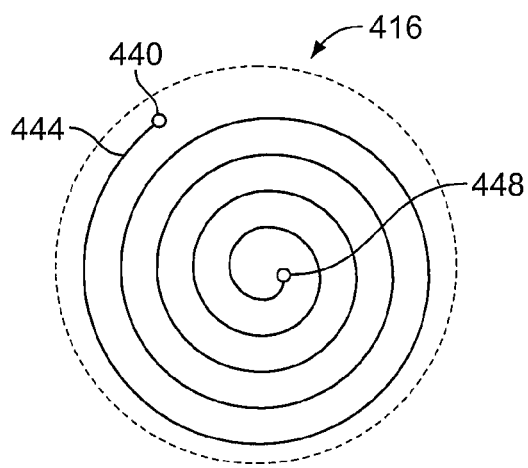

Alternately still, as see in FIGS. 9A and 9B, the groove 444 can be formed as a flat spiral in, for example, a split disk 416 or other element. An inlet 440 into the groove 444 can be formed in a top or side (not shown) of the disk 416 with an outlet 448 open to the chamber 436.

Figure 10:
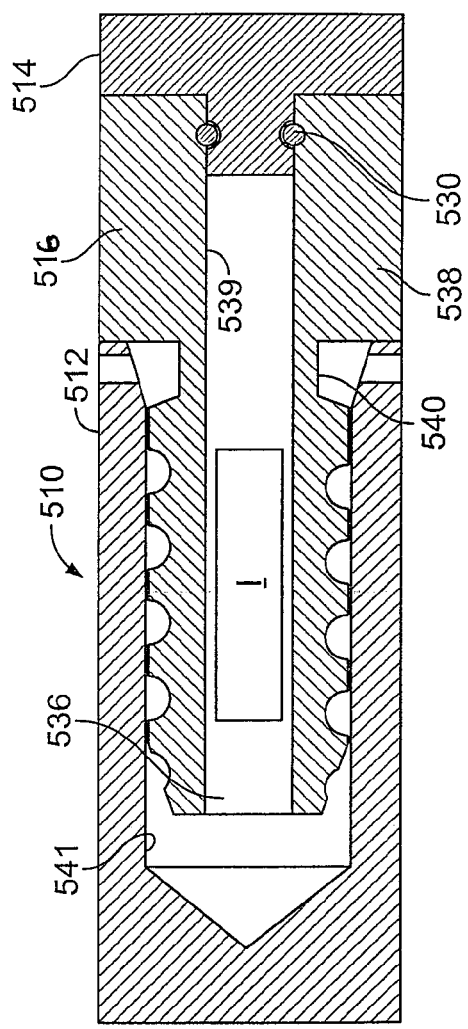
FIG. 10 is a cross-sectional view of an alternate embodiment of the sterilization challenge specimen holder.
Figure 11:
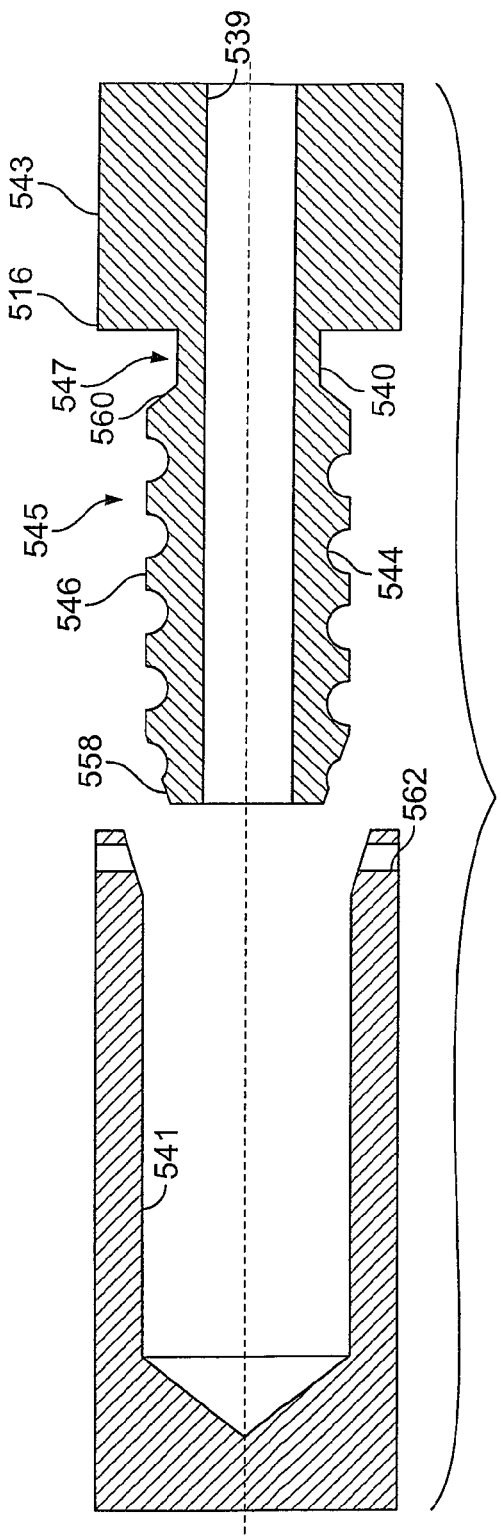
FIG. 11 is an exploded view of the body and plug of the holder of FIG. 10.

Yet another embodiment of the holder 510 is illustrated in FIGS. 10 and 11. In this embodiment, the end plug 516 is fitted into the holder body 512. The plug 516 has a body 538 that includes a central bore 539 that defines, in part and with the holder body 512, the holder chamber 536. The plug 516 provides a single ingress and egress flow path into and out of the holder chamber 536 when the cap 514 is in place on the holder 510 and permits drawing a vacuum and introducing steam into to the holder chamber 536. As illustrated, the indicator 1 resides in the plug bore 539 or between the plug bore 536 and the body interior 541.

The plug body 538 has an end portion 543 and a depending portion 545 having an outer wall 546 in which the spiral formed channel or groove 544 is formed. The groove 544 is contiguous with a circumferential recess or well 540 at an inlet side 547 and opens to the interior chamber 536 (formed with the body 512). Chamfers 558, 560 at both ends of the depending portion 545 provide for a smooth transition into and out of the groove 544 and prevent excessive resistance to flow through the groove 544.

The chamber body 512 includes one or more openings 562 (e.g., ⅛ inch through-wall openings) in the side wall that are open to (and contiguous with) the plug recess 540. This provides the flow path for drawing vacuum in and introducing steam to the holder chamber 536.

The end cap 514 can be formed to friction (or push) fit into the plug bore 539, or alternately (although not shown), threadedly engage the plug 516. A seal 530 is present at the end cap 514/plug 516 interface.

A present holder 10 is formed from aluminum. Many different materials are contemplated for use, including various other metals, steels, alloys and the like. Suitable polymers may also be used, as will be appreciated by those skilled in the art. Due to the thermal conditions to which the holder 10 is subjected, each of the parts of the present holder 10 (the body 12, the cap 14 and the plug 16) is preferably formed from a similar material. This is to prevent the parts from expanding and contracting at different rates, and in different proportions from one another. It is also contemplated that different materials having similar thermal properties can also be used, where appropriate.

In one method of fitting the plug 16 into the body 12, advantage is taken of the thermal expansion coefficient of the material or materials used to make the holder 10. It will be appreciated that the groove 44 cannot be blocked, such as by debris, otherwise the resistance or challenge characteristics of the holder 10 will not be consistent from one holder 10 to the next, nor properly predictable. Accordingly, in order to fit or position the plug 16 in the body 12, the body 12 is heated to expand and the plug 16 is inserted into the heated body 12. If necessary, the plug 16 can be cooled to contract or shrink, so that the plug 16 easily fits into the body 12 without deformation of either part.

Figure 12:
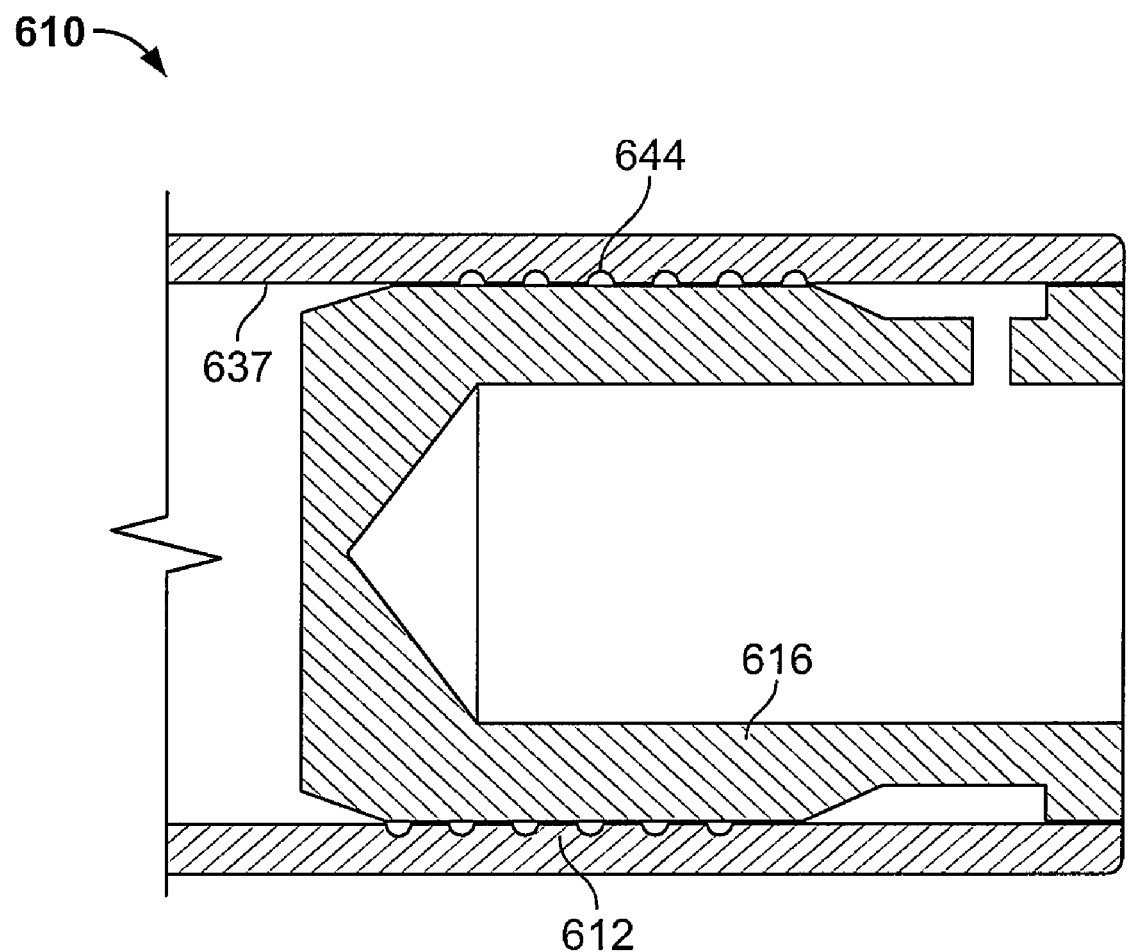
FIG. 12 is a partial cross-sectional view of an alternate specimen holder showing the groove formed in the body and a smooth-walled plug.

It will also be appreciated from the above-provided discussion that the spiral groove 44 must be formed or machined to within a fairly tight tolerance. In a present holder 10, a plug 16 having an overall length $l_{16}$ of about one inch is formed with a groove 44 having a cross-sectional area $A_{44}$ of 0.00031 inches$^2$. The groove 44 is formed using a ¹⁄₁₆ inch grooving tool having a rounded or curved profile, and cut to a depth $d_{44}$ of about 0.011 inches +/−0.0005 inches (about ⅓ of a circle having a ¹⁄₁₆ inch diameter). The groove 44 has width $w_{44}$ of about 0.045 inches. Cross-sectional areas of up to about 0.001 inches$^2$ can be used, however, the length $l_{16}$ of the plug 16 (and the spiral groove 44) is formed commensurately longer. For example, in a groove 44 having a cross-sectional area of 0.000553 inches$^2$, the groove 44 must be formed in a plug 16 having a length $l_{16}$ of about 2 inches (compared to a 1 inch plug 16 for the 0.00031 inch$^2$ area). It has been found that the cross-sectional area of the groove 44 is best formed at less than about 5.5 E-4 inches$^2$. The grooves 44 are formed in the plug 16 at a rate (density) of about 10 turns per linear inch of plug 16. Referring briefly to FIG. 12, it will be appreciated that the groove 644 can be formed in the interior wall 637 of the holder body 612 and the plug 616 can be a smooth-walled or smooth surface element.

In a sterilization process, the objects to be sterilized are placed in a closed environment (sterilization chamber or device) and the air is evacuated from the device. Steam S is then introduced into the device at a predetermined temperature (pressure) for a predetermined period of time. The environment is first evacuated for a number of reasons. First, is so that the steam does not have to compete with the air for volume within the holder 10. Second, is so that the steam flows more readily into the holder 10 without having to displace the air. In addition, there is less heat (energy) transfer from the steam in that there is no air (no mass) to which to transfer the energy from the steam.

In a typical use, a strip or other indicator I (specimen) is placed in the holder 10 and the holder 10 is placed inside of the sterilization device along with the items to be sterilized, such as towels, gowns or the like. The device is evacuated and is steam is then introduced into the device. Following a predetermined sterilization protocol, the items (that are now sterilized) are removed from the device, as is the specimen holder 10. The indicator I is then tested to determine the kill rate of the spores on or in the indicator.

The sterilization process may be carried out a number of times (e.g., in a pulsed or multi-pulsed manner), in which the air is evacuated, steam is introduced, device evacuated, steam introduced, and so on. Following completion of the cycles, the indicator or specimen I is tested for spore kill rate.

It will be appreciated that the greater a challenge is to the sterilization process, the lower the kill rate. That is, the greater the challenge, the more difficult it is for steam to infiltrate (more difficult entry) and thus a lower kill rate results.

Samples of the present holder 10, an Association for the Advancement of Medical Instrumentation (AAMI) towel pack, and a 3M Attest biological test pack were tested in order to determine the effectiveness of the challenge. The indicator in each case was a 3M Attest 1262 biological indicator.

In each test, the sample was placed in the device and the device was evacuated (a negative pressure drawn to 1 psia).

Steam, at about saturated conditions, was then introduced into the device at a temperature of about 270° F. for times of 15 seconds, 1, 2, 3 and 4 minutes. Thirty (30) separate samples were used of the AAMI towel pack and the present holder at each of the selected times (for the present holder at 15 seconds, 29 samples were used), and six (6) separate samples of a test pack were used at each of the selected times.

Table 1, below, shows the number of positives (live biological activity) that remained in each of the samples following the sterilization procedure.

TABLE 1

Various Challenge Samples with Positive Biological Activity at Varying Sterilization Times

| Time | Towel Pack | Test Pack | Present Holder |
|---|---|---|---|
| 15 sec. | 30/30 | 6/6 | 29/29 |
| 1 min. | 6/30 | 0/6 | 23/30 |
| 2 min. | 0/30 | 0/6 | 14/30 |
| 3 min. | 0/30 | 0/6 | 5/30 |
| 4 min | 0/30 | 0/6 | 0/30 |

As can be seen from the results in Table 1, biological activity was present in the samples in the present holder at 3 minutes in 5 of 30 samples, and was only completely eliminated at 4 minutes, whereas in each the towel pack and the 3M Attest Pack, biological activity was completely eliminated by 2 minutes and 1 minute, respectively. In fact, at 2 minutes, biological activity using the present holder was present in almost 50 percent of the samples.

It was also found that by adding a layer of an insulator 18 over the body 12, the challenge was increased. The insulating layer 18 (which can be, for example, a layer of neoprene or the like) reduces heat transfer through the tubular wall body 12 and thus reduces the heating effect inside of the chamber 36 that occurs by way of conduction through the body 12 wall. As such the heating that occurs inside of the chamber 36 is due to the introduction of steam by way of the spiral groove 44. The insulation can, of course, be disposed on any part of, or the entirety of the holder 10 (e.g., on any part or all of the body 12, cap 14 and plug 16), so long as the steam flow path is maintained open.

All patents referred to herein, are hereby incorporated herein by reference, whether or not specifically do so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A sterilization challenge specimen holder comprising: a rigid body having an internal chamber region; a rigid cap sealable on a first end of the body; and a rigid plug positioned in a second end of the body, the plug providing an external seal between the environs and the body and having an outer wall having a spiral formed groove therein in communication with the internal chamber region, the plug having an opening therein for defining a single flow path for communication between the environs and the internal chamber via the spiral formed groove.

2. The sterilization challenge specimen holder in accordance with claim 1 wherein the body has a thread on the first end for mating with a thread in the cap.

3. The sterilization challenge specimen holder in accordance with claim 1 wherein the body has a smooth inner wall at the second end.

4. The sterilization challenge specimen holder in accordance with claim 1 wherein the groove is formed having a rounded cross-sectional profile.

5. The sterilization challenge specimen holder in accordance with claim 4 wherein the groove has a cross-sectional area of less than 5.5 E-4 in$^2$.

6. The sterilization challenge specimen holder in accordance with claim 1 wherein the plug includes a chamfer at an end of the plug innermost of the internal chamber region, and wherein a lower end of the spiral formed groove terminates at the chamfer.

7. The sterilization challenge specimen holder in accordance with claim 1 wherein the plug includes a well formed therein, the well defining a wall in the plug and being open to the environs, and wherein the plug includes an opening in the wall for communication between the environs and the internal chamber region through the groove.

8. The sterilization challenge specimen holder in accordance with claim 7 including a recess formed in an inner surface of the wall, the recess defining a sealing lip between the recess and the environs and wherein the opening in the wall opens into the recess.

9. The sterilization challenge specimen holder in accordance with claim 8 including a chamfer in the recess, and wherein an upper end of the spiral formed groove terminates at the chamfer.

10. The sterilization challenge specimen holder in accordance with claim 1 wherein the plug and the body are formed from like materials.

11. The sterilization challenge specimen holder in accordance with claim 10 wherein the material is aluminum.

12. The sterilization challenge specimen holder in accordance with claim 1 wherein the cap has a knurled edge and a flat region on the edge.

13. The sterilization challenge specimen holder in accordance with claim 1 including an insulating layer on at least a portion thereof.

14. A sterilization challenge specimen holder comprising: a rigid body having an internal chamber region; a rigid plug positioned in part in the body, the plug providing an external seal between the environs and the body and having a central bore and having an outer wall having a spiral formed groove therein in communication with the internal chamber region, wherein the body has an opening therein for defining a single flow path for communication between the environs and the internal chamber via the spiral formed groove; and a rigid cap sealable on the plug.

15. The sterilization challenge specimen holder in accordance with claim 14 wherein the plug includes a well formed therein at an end of the spiral formed groove, and wherein the body opening opens into the plug well to provide communication between the environs and the internal chamber region through the groove.

16. The sterilization challenge specimen holder in accordance with claim 14 wherein the groove is formed having a rounded cross-sectional profile.

17. The sterilization challenge specimen holder in accordance with claim 14 wherein the groove has a cross-sectional area of less than 5.5 E-4 in$^2$.

18. The sterilization challenge specimen holder in accordance with claim 14 including an insulating layer on at least a portion thereof.

19. The sterilization challenge specimen holder in accordance with claim 14 including a pressure reducing element disposed in the flow path for communication from the environs into the internal chamber.

* * * * *

UNITED STATES PATENT AND TRADEMARK OFFICE
CERTIFICATE OF CORRECTION

| | | |
|---|---|---|
| PATENT NO. | : 7,718,125 B2 | Page 1 of 1 |
| APPLICATION NO. | : 11/828202 | |
| DATED | : May 18, 2010 | |
| INVENTOR(S) | : Harry Bala | |

It is certified that error appears in the above-identified patent and that said Letters Patent is hereby corrected as shown below:

Column 2, line 26: The word "The" should be replaced with "To" and should read "To facilitate handling..."

Column 2, line 32: The word "reduced" should be replaced with "reduce"

Column 2, line 35: A --,-- should be inserted after the word "flat" and before the word "split" and should read "...as a flat, split disk-..."

Column 2, line 63: The ";" should be replaced with ":"

Column 3, line 49: The word "be" should be added and should read "the illustrated O-ring can be fitted onto the cap 14 and the body 12."

Column 6, line 13: The word "is" should be removed before the word "steam"

Signed and Sealed this

Ninth Day of November, 2010

David J. Kappos
*Director of the United States Patent and Trademark Office*